US005756085A

United States Patent [19]
Sykes et al.

[11] Patent Number: 5,756,085
[45] Date of Patent: *May 26, 1998

[54] USE OF INTERLEUKIN-12 TO PREVENT GRAFT VERSUS HOST DISEASE

[75] Inventors: Megan Sykes, Charlestown; Stanley F. Wolf, Arlington, both of Mass.

[73] Assignees: Genetics Institute, Inc., Cambridge; The General Hospital Corporation, Boston, both of Mass.

[ * ] Notice: The term of this patent shall not extend beyond the expiration date of Pat. No. 5,573,764.

[21] Appl. No.: 640,386

[22] Filed: Apr. 30, 1996

Related U.S. Application Data

[63] Continuation-in-part of Ser. No. 186,529, Jan. 21, 1994, Pat. No. 5,573,764.

[51] Int. Cl.$^6$ .................................... A61K 45/05
[52] U.S. Cl. .................................... 424/85.2; 514/21
[58] Field of Search .................... 424/85.2; 514/21

[56] References Cited

U.S. PATENT DOCUMENTS 5,573,764 11/1996 Sykes et al. .................... 424/85.2

FOREIGN PATENT DOCUMENTS 0 625 354 A1 12/1994 European Pat. Off. .
WO 93/17698 9/1993 WIPO .

OTHER PUBLICATIONS

Gaddy, J. et al., J. Immunol. 150:96 A (1993).
Azuma, E. et al., J. Immunol. 143:1524-1529 (1989).
Klimpel, G. et al., J. Immunol. 144:84-93 (1990).
Niederwieser, D. et al., Transplantation 50:620-625 (1990).
Troutt, A. et al., PNAS 89:5276-5280 (1992).
Mowat, A., Immunology 68:18-23 (1989).
Allen, R. et al., Eur. J. Immunol. 23:333-337 (1993).
Brok, H.P.M. et al., J. Immunol. 151:6451-6459 (1993).
Jadus, M. et al., Bone Marrow Transplant 10:1-14 (1992).
Antin, J. et al., Blood 80:2964-2968 (1992).
Dickinson, A. et al., Bone Marrow Transplant 7:209-216 (1991).
Parkman, R. et al., J. Cell Biochem. 16(a):186 (1992).
Thiele, D. et al., J. Immunol. 138:51-57 (1987).
Piguet, P. et al., J. Exp. Med. 166:1280-1289 (1987).
Holler, E. et al., Blood 75:1011-1016 (1990).
Holler, E. et al., Transplant Proc. 25:1234-1236 (1993).
Shalaby, M. et al., Transplantation 47:1057-1061 (1989).
Soiffer et al., Blood, vol. 82(9) pp. 2790-96, Nov. 1993.
Jacobsen et al., J. Exp. Med., vol. 178, pp. 413-18, Aug. 1993.
Chan et al., J. Exp Med., vol. 173, pp. 869-879, 1991.
The Economist, "Panic in the Petri Dish", pp. 61-62, Jul., 1994.
Cross et al., Infection and Immunity, vol. 61(7), pp. 2741-2747, Jul. 1993.
Osband et al., Immunology Today, vol. 11(6), pp. 193-195, 1990.
Waldmann et al., Science, vol. 252, pp. 1657-1662, Jun. 1991.
Sykes et al., J. Exp. Med., vol. 171, pp. 645-658, 1990.
Sykes et al., PNAS, vol. 87, pp. 5633-5637, 1990.
Sykes et al., J. Imunol., vol. 150(1), pp. 197-205, Jan. 1993.
Cesano et al., Progress in Clinical and Biological Research 389:165-173 (1994).
Via et al., Arthritis and Rheumatism, 36(9):263 (1993).
Soiffer et al., Blood 82(9):2790-2796 (1993).
Azuma et al., J. Immunol., vol. 143(5), pp. 1524-1529, Sep. 1989.
Gately et al., Cell. Immunol., vol. 143, pp. 127-142, 1992.
Via et al., J. Immunol. 153:4040-4047 (1994).

*Primary Examiner*—Chhaya D. Sayala
*Attorney, Agent, or Firm*—Scott A. Brown; Thomas J. DesRosier

[57] ABSTRACT

The use of interleukin-12 to prevent, to ameliorate, and to treat graft-versus-host disease in a mammal in need of such treatment is disclosed. In other embodiments, graft-vs. leukemia effects are maintained or promoted.

13 Claims, 6 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 987 base pairs
        ( B ) TYPE: nucleic acid
        ( C ) STRANDEDNESS: single
        ( D ) TOPOLOGY: linear     ( i i ) MOLECULE TYPE: cDNA     ( v i ) ORIGINAL SOURCE:
        ( A ) ORGANISM: Homo sapiens
        ( G ) CELL TYPE: Lymphoblast
        ( H ) CELL LINE: RPMI 8866

( i x ) FEATURE:
        ( A ) NAME/KEY: CDS
        ( B ) LOCATION: 1..987

( x i ) SEQUENCE DESCRIPTION: SEQ ID NO:1:

```
ATG  TGT  CAC  CAG  CAG  TTG  GTC  ATC  TCT  TGG  TTT  TCC  CTG  GTT  TTT  CTG     48
Met  Cys  His  Gln  Gln  Leu  Val  Ile  Ser  Trp  Phe  Ser  Leu  Val  Phe  Leu
 1                   5                        10                       15

GCA  TCT  CCC  CTC  GTG  GCC  ATA  TGG  GAA  CTG  AAG  AAA  GAT  GTT  TAT  GTC     96
Ala  Ser  Pro  Leu  Val  Ala  Ile  Trp  Glu  Leu  Lys  Lys  Asp  Val  Tyr  Val
                    20                       25                       30

GTA  GAA  TTG  GAT  TGG  TAT  CCG  GAT  GCC  CCT  GGA  GAA  ATG  GTG  GTC  CTC    144
Val  Glu  Leu  Asp  Trp  Tyr  Pro  Asp  Ala  Pro  Gly  Glu  Met  Val  Val  Leu
               35                       40                       45

ACC  TGT  GAC  ACC  CCT  GAA  GAA  GAT  GGT  ATC  ACC  TGG  ACC  TTG  GAC  CAG    192
Thr  Cys  Asp  Thr  Pro  Glu  Glu  Asp  Gly  Ile  Thr  Trp  Thr  Leu  Asp  Gln
          50                       55                       60
```

| | | | | | | | | | | | | | | | | |
|---|---|---|---|---|---|---|---|---|---|---|---|---|---|---|---|---|
| AGC | AGT | GAG | GTC | TTA | GGC | TCT | GGC | AAA | ACC | CTG | ACC | ATC | CAA | GTC | AAA | 240 |
| Ser | Ser | Glu | Val | Leu | Gly | Ser | Gly | Lys | Thr | Leu | Thr | Ile | Gln | Val | Lys | |
| 65 | | | | 70 | | | | | 75 | | | | | | 80 | |
| GAG | TTT | GGA | GAT | GCT | GGC | CAG | TAC | ACC | TGT | CAC | AAA | GGA | GGC | GAG | GTT | 288 |
| Glu | Phe | Gly | Asp | Ala | Gly | Gln | Tyr | Thr | Cys | His | Lys | Gly | Gly | Glu | Val | |
| | | | | 85 | | | | | 90 | | | | | 95 | | |
| CTA | AGC | CAT | TCG | CTC | CTG | CTG | CTT | CAC | AAA | AAG | GAA | GAT | GGA | ATT | TGG | 336 |
| Leu | Ser | His | Ser | Leu | Leu | Leu | Leu | His | Lys | Lys | Glu | Asp | Gly | Ile | Trp | |
| | | | 100 | | | | | 105 | | | | | 110 | | | |
| TCC | ACT | GAT | ATT | TTA | AAG | GAC | CAG | AAA | GAA | CCC | AAA | AAT | AAG | ACC | TTT | 384 |
| Ser | Thr | Asp | Ile | Leu | Lys | Asp | Gln | Lys | Glu | Pro | Lys | Asn | Lys | Thr | Phe | |
| | | 115 | | | | 120 | | | | | 125 | | | | | |
| CTA | AGA | TGC | GAG | GCC | AAG | AAT | TAT | TCT | GGA | CGT | TTC | ACC | TGC | TGG | TGG | 432 |
| Leu | Arg | Cys | Glu | Ala | Lys | Asn | Tyr | Ser | Gly | Arg | Phe | Thr | Cys | Trp | Trp | |
| | 130 | | | | | 135 | | | | | 140 | | | | | |
| CTG | ACG | ACA | ATC | AGT | ACT | GAT | TTG | ACA | TTC | AGT | GTC | AAA | AGC | AGC | AGA | 480 |
| Leu | Thr | Thr | Ile | Ser | Thr | Asp | Leu | Thr | Phe | Ser | Val | Lys | Ser | Ser | Arg | |
| 145 | | | | | 150 | | | | | 155 | | | | | 160 | |
| GGC | TCT | TCT | GAC | CCC | CAA | GGG | GTG | ACG | TGC | GGA | GCT | GCT | ACA | CTC | TCT | 528 |
| Gly | Ser | Ser | Asp | Pro | Gln | Gly | Val | Thr | Cys | Gly | Ala | Ala | Thr | Leu | Ser | |
| | | | | 165 | | | | | 170 | | | | | 175 | | |
| GCA | GAG | AGA | GTC | AGA | GGG | GAC | AAC | AAG | GAG | TAT | GAG | TAC | TCA | GTG | GAG | 576 |
| Ala | Glu | Arg | Val | Arg | Gly | Asp | Asn | Lys | Glu | Tyr | Glu | Tyr | Ser | Val | Glu | |
| | | | 180 | | | | | 185 | | | | | 190 | | | |
| TGC | CAG | GAG | GAC | AGT | GCC | TGC | CCA | GCT | GCT | GAG | GAG | AGT | CTG | CCC | ATT | 624 |
| Cys | Gln | Glu | Asp | Ser | Ala | Cys | Pro | Ala | Ala | Glu | Glu | Ser | Leu | Pro | Ile | |
| | | 195 | | | | | 200 | | | | | 205 | | | | |
| GAG | GTC | ATG | GTG | GAT | GCC | GTT | CAC | AAG | CTC | AAG | TAT | GAA | AAC | TAC | ACC | 672 |
| Glu | Val | Met | Val | Asp | Ala | Val | His | Lys | Leu | Lys | Tyr | Glu | Asn | Tyr | Thr | |
| | 210 | | | | | 215 | | | | | 220 | | | | | |
| AGC | AGC | TTC | TTC | ATC | AGG | GAC | ATC | ATC | AAA | CCT | GAC | CCA | CCC | AAG | AAC | 720 |
| Ser | Ser | Phe | Phe | Ile | Arg | Asp | Ile | Ile | Lys | Pro | Asp | Pro | Pro | Lys | Asn | |
| 225 | | | | | 230 | | | | | 235 | | | | | 240 | |
| TTG | CAG | CTG | AAG | CCA | TTA | AAG | AAT | TCT | CGG | CAG | GTG | GAG | GTC | AGC | TGG | 768 |
| Leu | Gln | Leu | Lys | Pro | Leu | Lys | Asn | Ser | Arg | Gln | Val | Glu | Val | Ser | Trp | |
| | | | | 245 | | | | | 250 | | | | | 255 | | |
| GAG | TAC | CCT | GAC | ACC | TGG | AGT | ACT | CCA | CAT | TCC | TAC | TTC | TCC | CTG | ACA | 816 |
| Glu | Tyr | Pro | Asp | Thr | Trp | Ser | Thr | Pro | His | Ser | Tyr | Phe | Ser | Leu | Thr | |
| | | | 260 | | | | | 265 | | | | | 270 | | | |
| TTC | TGC | GTT | CAG | GTC | CAG | GGC | AAG | AGC | AAG | AGA | GAA | AAG | AAA | GAT | AGA | 864 |
| Phe | Cys | Val | Gln | Val | Gln | Gly | Lys | Ser | Lys | Arg | Glu | Lys | Lys | Asp | Arg | |
| | | 275 | | | | | 280 | | | | | 285 | | | | |
| GTC | TTC | ACG | GAC | AAG | ACC | TCA | GCC | ACG | GTC | ATC | TGC | CGC | AAA | AAT | GCC | 912 |
| Val | Phe | Thr | Asp | Lys | Thr | Ser | Ala | Thr | Val | Ile | Cys | Arg | Lys | Asn | Ala | |
| | 290 | | | | | 295 | | | | | 300 | | | | | |
| AGC | ATT | AGC | GTG | CGG | GCC | CAG | GAC | CGC | TAC | TAT | AGC | TCA | TCT | TGG | AGC | 960 |
| Ser | Ile | Ser | Val | Arg | Ala | Gln | Asp | Arg | Tyr | Tyr | Ser | Ser | Ser | Trp | Ser | |
| 305 | | | | | 310 | | | | | 315 | | | | | 320 | |
| GAA | TGG | GCA | TCT | GTG | CCC | TGC | AGT | TAG | | | | | | | | 987 |
| Glu | Trp | Ala | Ser | Val | Pro | Cys | Ser | | | | | | | | | |
| | | | | 325 | | | | | | | | | | | | |

( 2 ) INFORMATION FOR SEQ ID NO:2:

( i ) SEQUENCE CHARACTERISTICS:
        ( A ) LENGTH: 328 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met Cys His Gln Gln Leu Val Ile Ser Trp Phe Ser Leu Val Phe Leu
 1               5                  10                 15
Ala Ser Pro Leu Val Ala Ile Trp Glu Leu Lys Lys Asp Val Tyr Val
            20                  25                 30
Val Glu Leu Asp Trp Tyr Pro Asp Ala Pro Gly Glu Met Val Val Leu
        35                  40                 45
Thr Cys Asp Thr Pro Glu Glu Asp Gly Ile Thr Trp Thr Leu Asp Gln
    50                  55                 60
Ser Ser Glu Val Leu Gly Ser Gly Lys Thr Leu Thr Ile Gln Val Lys
 65             70                  75                     80
Glu Phe Gly Asp Ala Gly Gln Tyr Thr Cys His Lys Gly Gly Glu Val
                85                  90                 95
Leu Ser His Ser Leu Leu Leu Leu His Lys Lys Glu Asp Gly Ile Trp
            100                 105                110
Ser Thr Asp Ile Leu Lys Asp Gln Lys Glu Pro Lys Asn Lys Thr Phe
        115                 120                125
Leu Arg Cys Glu Ala Lys Asn Tyr Ser Gly Arg Phe Thr Cys Trp Trp
    130                 135                140
Leu Thr Thr Ile Ser Thr Asp Leu Thr Phe Ser Val Lys Ser Ser Arg
145                 150                 155                160
Gly Ser Ser Asp Pro Gln Gly Val Thr Cys Gly Ala Ala Thr Leu Ser
                165                 170                175
Ala Glu Arg Val Arg Gly Asp Asn Lys Glu Tyr Glu Tyr Ser Val Glu
            180                 185                190
Cys Gln Glu Asp Ser Ala Cys Pro Ala Ala Glu Glu Ser Leu Pro Ile
        195                 200                205
Glu Val Met Val Asp Ala Val His Lys Leu Lys Tyr Glu Asn Tyr Thr
    210                 215                220
Ser Ser Phe Phe Ile Arg Asp Ile Ile Lys Pro Asp Pro Pro Lys Asn
225                 230                 235                240
Leu Gln Leu Lys Pro Leu Lys Asn Ser Arg Gln Val Glu Val Ser Trp
                245                 250                255
Glu Tyr Pro Asp Thr Trp Ser Thr Pro His Ser Tyr Phe Ser Leu Thr
            260                 265                270
Phe Cys Val Gln Val Gln Gly Lys Ser Lys Arg Glu Lys Lys Asp Arg
        275                 280                285
Val Phe Thr Asp Lys Thr Ser Ala Thr Val Ile Cys Arg Lys Asn Ala
    290                 295                300
Ser Ile Ser Val Arg Ala Gln Asp Arg Tyr Tyr Ser Ser Ser Trp Ser
305                 310                 315                320
Glu Trp Ala Ser Val Pro Cys Ser
                325
```

( 2 ) INFORMATION FOR SEQ ID NO:3:

( i ) SEQUENCE CHARACTERISTICS:
        ( A ) LENGTH: 660 base pairs
        ( B ) TYPE: nucleic acid
        ( C ) STRANDEDNESS: single
        ( D ) TOPOLOGY: linear     ( i i ) MOLECULE TYPE: cDNA     ( v i ) ORIGINAL SOURCE:
        ( A ) ORGANISM: Homo sapiens
        ( G ) CELL TYPE: Lymphoblast
        ( H ) CELL LINE: RPMI 8866

( i x ) FEATURE:
    ( A ) NAME/KEY: CDS
    ( B ) LOCATION: 1..660

( x i ) SEQUENCE DESCRIPTION: SEQ ID NO:3:

```
ATG TGT CCA GCG CGC AGC CTC CTC CTT GTG GCT ACC CTG GTC CTC CTG      48
Met Cys Pro Ala Arg Ser Leu Leu Leu Val Ala Thr Leu Val Leu Leu
 1               5                  10                  15

GAC CAC CTC AGT TTG GCC AGA AAC CTC CCC GTG GCC ACT CCA GAC CCA      96
Asp His Leu Ser Leu Ala Arg Asn Leu Pro Val Ala Thr Pro Asp Pro
             20                  25                  30

GGA ATG TTC CCA TGC CTT CAC CAC TCC CAA AAC CTG CTG AGG GCC GTC     144
Gly Met Phe Pro Cys Leu His His Ser Gln Asn Leu Leu Arg Ala Val
         35                  40                  45

AGC AAC ATG CTC CAG AAG GCC AGA CAA ACT CTA GAA TTT TAC CCT TGC     192
Ser Asn Met Leu Gln Lys Ala Arg Gln Thr Leu Glu Phe Tyr Pro Cys
     50                  55                  60

ACT TCT GAA GAG ATT GAT CAT GAA GAT ATC ACA AAA GAT AAA ACC AGC     240
Thr Ser Glu Glu Ile Asp His Glu Asp Ile Thr Lys Asp Lys Thr Ser
 65                  70                  75                  80

ACA GTG GAG GCC TGT TTA CCA TTG GAA TTA ACC AAG AAT GAG AGT TGC     288
Thr Val Glu Ala Cys Leu Pro Leu Glu Leu Thr Lys Asn Glu Ser Cys
                 85                  90                  95

CTA AAT TCC AGA GAG ACC TCT TTC ATA ACT AAT GGG AGT TGC CTG GCC     336
Leu Asn Ser Arg Glu Thr Ser Phe Ile Thr Asn Gly Ser Cys Leu Ala
            100                 105                 110

TCC AGA AAG ACC TCT TTT ATG ATG GCC CTG TGC CTT AGT AGT ATT TAT     384
Ser Arg Lys Thr Ser Phe Met Met Ala Leu Cys Leu Ser Ser Ile Tyr
        115                 120                 125

GAA GAC TTG AAG ATG TAC CAG GTG GAG TTC AAG ACC ATG AAT GCA AAG     432
Glu Asp Leu Lys Met Tyr Gln Val Glu Phe Lys Thr Met Asn Ala Lys
130                 135                 140

CTT CTG ATG GAT CCT AAG AGG CAG ATC TTT CTA GAT CAA AAC ATG CTG     480
Leu Leu Met Asp Pro Lys Arg Gln Ile Phe Leu Asp Gln Asn Met Leu
145                 150                 155                 160

GCA GTT ATT GAT GAG CTG ATG CAG GCC CTG AAT TTC AAC AGT GAG ACT     528
Ala Val Ile Asp Glu Leu Met Gln Ala Leu Asn Phe Asn Ser Glu Thr
                165                 170                 175

GTG CCA CAA AAA TCC TCC CTT GAA GAA CCG GAT TTT TAT AAA ACT AAA     576
Val Pro Gln Lys Ser Ser Leu Glu Glu Pro Asp Phe Tyr Lys Thr Lys
            180                 185                 190

ATC AAG CTC TGC ATA CTT CTT CAT GCT TTC AGA ATT CGG GCA GTG ACT     624
Ile Lys Leu Cys Ile Leu Leu His Ala Phe Arg Ile Arg Ala Val Thr
        195                 200                 205

ATT GAT AGA GTG ATG AGC TAT CTG AAT GCT TCC TAA                     660
Ile Asp Arg Val Met Ser Tyr Leu Asn Ala Ser
210                 215                 220
```

( 2 ) INFORMATION FOR SEQ ID NO:4:

( i ) SEQUENCE CHARACTERISTICS:
        ( A ) LENGTH: 219 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:4:

```
Met Cys Pro Ala Arg Ser Leu Leu Leu Val Ala Thr Leu Val Leu Leu
 1               5                  10                  15

Asp His Leu Ser Leu Ala Arg Asn Leu Pro Val Ala Thr Pro Asp Pro
             20                  25                  30
```

| Gly | Met | Phe 35 | Pro | Cys | Leu | His | His 40 | Ser | Gln | Asn | Leu | Leu 45 | Arg | Ala | Val |
|---|---|---|---|---|---|---|---|---|---|---|---|---|---|---|---|
| Ser | Asn 50 | Met | Leu | Gln | Lys | Ala 55 | Arg | Gln | Thr | Leu | Glu 60 | Phe | Tyr | Pro | Cys |
| Thr 65 | Ser | Glu | Glu | Ile | Asp 70 | His | Glu | Asp | Ile | Thr 75 | Lys | Asp | Lys | Thr | Ser 80 |
| Thr | Val | Glu | Ala | Cys 85 | Leu | Pro | Leu | Glu | Leu 90 | Thr | Lys | Asn | Glu | Ser 95 | Cys |
| Leu | Asn | Ser | Arg 100 | Glu | Thr | Ser | Phe | Ile 105 | Thr | Asn | Gly | Ser | Cys 110 | Leu | Ala |
| Ser | Arg | Lys 115 | Thr | Ser | Phe | Met | Met 120 | Ala | Leu | Cys | Leu | Ser 125 | Ser | Ile | Tyr |
| Glu | Asp 130 | Leu | Lys | Met | Tyr | Gln 135 | Val | Glu | Phe | Lys | Thr 140 | Met | Asn | Ala | Lys |
| Leu 145 | Leu | Met | Asp | Pro | Lys 150 | Arg | Gln | Ile | Phe | Leu 155 | Asp | Gln | Asn | Met | Leu 160 |
| Ala | Val | Ile | Asp | Glu 165 | Leu | Met | Gln | Ala | Leu 170 | Asn | Phe | Asn | Ser | Glu 175 | Thr |
| Val | Pro | Gln | Lys 180 | Ser | Ser | Leu | Glu | Glu 185 | Pro | Asp | Phe | Tyr | Lys 190 | Thr | Lys |
| Ile | Lys | Leu 195 | Cys | Ile | Leu | Leu | His 200 | Ala | Phe | Arg | Ile | Arg 205 | Ala | Val | Thr |
| Ile | Asp 210 | Arg | Val | Met | Ser | Tyr 215 | Leu | Asn | Ala | Ser | | | | | |

USE OF INTERLEUKIN-12 TO PREVENT GRAFT VERSUS HOST DISEASE

This application is a continuation-in-part of application Ser. No. 08/186,529, filed Jan. 21, 1994 now U.S. Pat. No. 5,573,764.

BACKGROUND OF THE INVENTION

The present invention relates to the field of prevention and treatment of graft-versus-host disease using interleukin-12, including the maintenance of graft-vs.-leukemia effects while providing such prevention or treatment.

An individual mammal's immune system functions through recognition of certain cell surface proteins, some of which are termed major histocompatibility complex proteins, or MHC proteins. Additional minor histocompatibility proteins exist which can also contribute to immunological recognition events. The individual mammal's immune system recognizes its own MHC proteins, or those of its identical twin, as self and thus does not destroy its own cells or those of its identical twin. Members of the same species may share major and/or minor histocompatibility antigens, and thus an individual may not recognize the cells of another member of its species as non-self, depending on the degree of the differences between the MHC proteins of the two individuals. When an individual's immune system recognizes the cells of other members of the same species as non-self, the first individual's immune system may proceed to destroy the cells of the second individual. In humans, the major histocompatibility proteins are known as "HLA" antigens.

When tissues such as bone marrow, blood cells, or solid organs are transplanted from one individual to another, normally the recipient will recognize the donor's cells as non-self and the recipient's immune system will destroy the donor's cells as described above. For this reason, in a tissue transplantation, the recipient is normally subjected to immunosuppressive drugs and/or irradiation. However, transplantation patients are also subject to immunologic recognition in the opposite direction, that is, the donor tissue may contain immunologically competent cells which proceed to destroy the recipient's cells, a condition termed "graft-versus-host disease" or "GVHD".

At the present time, many leukemia and lymphoma patients are treated by bone marrow transplantation. When an identical twin is available, such transplantation is termed "syngeneic" since the genetic characteristics of donor and recipient are identical. More frequently, bone marrow transplantations are "allogeneic", that is, the bone marrow which is transplanted is donated by an individual whose genetic characteristics differ from those of the recipient, especially as regards the MHC and minor histocompatibility antigens expressed on the surfaces of each individual's cells. Allogeneic bone marrow transplantation is being performed more and more frequently. In 1990, more than 4,000 such transplantations occurred. In recognition of the increasing need for bone marrow donors compatible with potential recipients, an international marrow donor registration system has been developed, in order to provide phenotypically matched marrow from unrelated donors.

Concomitant with the increasing frequency of allogeneic bone marrow transplantation, the incidence of potentially fatal complications such as graft-versus-host disease is also increasing.

Graft-versus-host disease can develop when bone marrow, blood products, or solid organs containing immunocompetent cells are transferred from a donor to a recipient. Thus, when MHC antigenic differences exist between the donor and recipient, the recipient is at risk for the development of graft-versus-host disease. Graft-versus-host disease may also develop when there are antigenic differences between donor and recipient for the minor histocompatibility antigens. Thus, graft-versus-host disease can also develop between MHC-matched persons. Moreover, surgery patients who receive directed blood transfusion, for example, transfusion of blood from an HLA homozygous child to a heterozygous parent, may also develop graft-versus-host disease.

Presently graft-versus-host disease is inhibited by attempting to eliminate immunocompetent donor cells, for example, by in vitro manipulation of the donor bone marrow. For example, immunocompetent T cells may be removed from the donor bone marrow through physical separation such as by lectin agglutination, or by treatment of the bone marrow with monoclonal antibodies directed to T cells. However, use of bone marrow depleted of T cells is associated with a higher rate of graft failure, which is frequently fatal. Use of T cell depleted bone marrow grafts is also associated with an increased incidence of relapse among the recipients, particularly recipients having chronic myelocytic leukemia.

In another approach, the recipient is subjected to immunosuppressive therapy after transplantation. Such immunosuppression may occur by use of glucocorticoids, cyclosporin, methotrexate, or combinations of such drugs. However, immunosuppression results in increased incidence of infection, and even when immunosuppressant drugs are used, graft-versus-host disease may still occur.

Although many approaches to controlling GVHD have been attempted, and a reduction of GVHD has been achieved with T-cell depletion (TCD) of donor bone marrow and the use of nonspecific immunosuppressive drugs, the rates of allograft failure and leukemic relapse are also increased by these approaches. Thus, the ideal clinically applicable approach to HLA-mismatched BMT would selectively inhibit the GVHD-promoting activity of allogeneic T cells while preserving allogeneic T cell-mediated graft-versus-leukemia (GVL) effects. When HLA non-genotypically identical unrelated donor transplants have been performed, increased GVHD has been at least partially offset by decreased leukemic relapse rates. Similar differences have been observed when single HLA antigen-mismatched transplants have been compared with HLA-identical transplants. These results indicate that GVL effects might be even greater if BMT could be performed in the setting of wider HLA mismatches. However, the full potential of this GVL effect cannot be exploited unless GVHD can, at the same time, be avoided.

Interleukin-12 is a heterodimeric cytokine which was originally identified as a factor which induces γ-interferon from T cells and natural killer cells as set forth in PCT/US91/06332, published Apr. 2, 1992, which is incorporated herein by reference. PCT/US91/06332 refers to interleukin-12 as Natural Killer Cell Stimulating Factor or NKSF. EP 433827, published Jun. 26, 1991 discloses interleukin-12 as a cytotoxic lymphocyte maturation factor (CLMF). The amino acid sequences of the human interleukin-12 subunits are set forth in SEQ ID NO: 1/SEQ ID NO: 2 (40 kD subunit) and SEQ ID NO: 3/SEQ ID NO: 4 (35 kD subunit).

Interleukin-12 also stimulates natural killer cells in vitro by increasing their ability to lyse target cells at a level comparable to that obtained with interferon-α and interleukin-2, well-known activators of natural killer cells' cytotoxic activity. Additional in vitro activities of interleukin-12 which have been identified include induction of T cell proliferation as a co-stimulant; suppression of interleukin-2 induced proliferation of natural killer blasts; suppression of interleukin-2 induced proliferation of T cell receptor-γδ-positive cells; promotion of Th1 T cell differentiation from progenitors; enhancement of Th1, but not Th2 proliferation; enhancement of T cell cytolytic activity; enhancement of cytotoxic lymphocyte generation; enhancement of natural killer and natural killer blast cytolytic activity; ex vivo enhancement of natural killer activity in peripheral blood mononuclear cells of interleukin-2-treated patients; induction of adhesion molecules on natural killer cells; induction of perforin and granzyme B mRNAs in natural killer blasts; induction of interleukin-2 receptor subunits (p55, p75) on natural killer cells; induction of low levels of tumor necrosis factor-α; suppression of IgE synthesis by interferon-γ-dependent and independent mechanisms; modulation of T cell development in fetal thymic organ cultures; and synergy with kit ligand to promote growth of myeloid and B cell progenitors. The known in vivo activities of interleukin-12 include induction of interferon-γ; enhancement of natural killer cell activity in spleen, liver, lungs and peritoneal cavity; enhancement of generation of allo-specific cytotoxic lymphocytes; induction of extramedullary hematopoiesis in mouse spleen; reversible suppression of hematopoiesis in bone marrow; reversible induction of anemia, lymphopenia, and neutropenia in mice; suppression of anti-IgD induced IgE, IgG1, and interleukin-4 expression; increased survival in SCID mice treated with *Toxoplasma gondii*; cure of leishmaniasis in susceptible strains of mice; decreased bioburden in cryptococcoses model; suppression of tumor growth; and promotion of immunity to tumor cells. Interleukin- 12 is also induced in vivo in the shwarzman reaction model of septic shock.

From the known activities of interleukin-12, it would be expected that treatment of mammals in allogeneic bone marrow transplantation would result in more severe graft-versus-host disease. Both interferon-γ and tumor necrosis factor-α, which are induced by interleukin-12 treatment, have been implicated in producing graft-versus-host disease. Furthermore, cytotoxic T-lymphocytes, whose generation is enhanced by interleukin-12, have also been implicated in graft-versus-host disease pathophysiology. Murine studies have shown that inhibition of a Th1 response by treatment with interleukin-2 is associated with inhibition of graft-versus-host disease. Therefore, enhancement of Th1 responses by treatment with interleukin-12 would be expected to increase the severity of graft-versus-host disease.

SUMMARY OF THE INVENTION

In one embodiment, the invention comprises a method of preventing graft-versus-host disease which comprises administering to a mammal, at the time of bone marrow transplantation, a therapeutically effective amount of interleukin-12.

In another embodiment, the invention comprises a method of ameliorating graft-versus-host disease which comprises administering to a mammal, at the time of bone marrow transplantation, a therapeutically effective amount of interleukin-12.

In yet another embodiment, the invention comprises a method of treating graft-versus-host disease which comprises administering to a mammal experiencing graft-versus-host disease a therapeutically effective amount of interleukin-12.

In preferred embodiments, the therapeutically effective amount is also effective to maintain or promote graft-vs.-leukemia effects in the mammal.

Methods are also provided for maintaining or promoting graft-vs.-leukemia effects which comprises administering to a mammal, at the time of bone marrow transplantation, a therapeutically effective amount of interleukin-12. Preferably, the therapeutically effective amount of interleukin-12 comprises 1 to 100 μg/kg body weight. In preferred embodiments, the therapeutic dose is also effective to prevent, ameliorate or treat graft-vs.-host disease resulting from such transplant.

BRIEF DESCRIPTION OF THE FIGURES

FIG. 2(A). Non-leukemic mice received $5 \times 10^6$ TCD B10 BMC and $15 \times 10^6$ B10 spleen cells alone with (n=3) or without IL-12 treatment (n=3) (Syn BMP +/−IL-12), or $5 \times 10^6$ TCD B10 BMC plus $10 \times 10^6$ A/J BMC and $15 \times 10^6$ A/J spleen cells with (Allo BMT+IL- 12) (n=8) or without (Allo BMT) IL-12 treatment (n=8). FIG. 2(B). Leukemic recipients in the same experiment received $5 \times 10^6$ TCD B10 BMC and $15 \times 10$ B10 spleen cells alone with (Syn BMO+EL4+IL-12) (n=5) or without (Syn BMT+EL4) IL-12 treatment (n=5), or $5 \times 10^6$ TCD BMC plus $10 \times 10^6$ A/J BMC and $15 \times 10^6$ A/J spleen cells with IL-12 treatment (Allo BMT+EL4+IL-12) (n=9). All leukemic recipients received 500 H-$2^b$ EL4 cells on the day of BMT.

FIG. 3. FACS profile showing mixed chimerism in lethally irradiated secondary recipients. B 10 mice received 10.25 Gy WBI, followed by transfer of B 10 TCD BMC plus TCD BMC and spleen cells from long-term (more than 100 days) surviving, IL-12 treated EL4 recipients (B10) of B 10 TCD BMC plus A/J BMC and spleen cells. WBC were prepared from these mice at 56 days after BMT, and were stained with FITC-labeled rat anti-mouse CD4 or CD8 mAbs along with biotinylated anti-mouse H-2D$^d$ mAb plus PEA.

FIGS. 4A and 4B. R4-6A2, a rat-mouse IFN-γ mAb, inhibits the protective effect of IL-12 against GVHD. Lethally irradiated B10 mice received $5 \times 10^6$ TCD B10 BMC plus $10 \times 10^6$ A/J BMC and $15 \times 10^6$ A/J spleen cells with no further treatment (Allo BMT, n=8), or with IL-12 (Allo BMT+IL-12, n=8) or R4-6A2 (Allo BMT+R4=6A2, n=5), or both (Allo BMT+IL-12+R4-6A2, n=8). Syngeneic controls received $5 \times 10^6$ TCD B10 BMC with treatments of IL-12 and R4-6A2 (SYN BMT+L-12+R4-6A2, n=3). 4,900 U IL-12 and 2.5 mg R4-6A2 were given by i.p. injection on day 0 and day 1 with respect to BMT, respectively.

BMC alone (Syn BMT) (□; n=3), or TCD B 10 BMC plus TCD A/J BMC and CD8-depleted A/J spleen cells with (CD8-dep. Allo BMT, L-12) (◊; n=5) or without IL-12 (Allo BMT) (○; n-5). Leukemic recipients receiving similar inocula plus EL4 cells are indicated as "Syn BMT, EL4" (★; n=5), "CD8-dep. Allo BMT, EL4) (■; n=8) and "CD8-dep. Allo BMT, EL4, IL-12" (●; n=8). One group received TCD B10 BMC plus TCD A/J BMC, TCD A/J spleen cells and EL4 with IL-12 (TCD Allo BMT, EL4, IL-12) (♦; n=8).

DETAILED DESCRIPTION OF THE INVENTION

The following abbreviations are used herein: BMC: bone marrow cells; BMT: bone marrow transplantation; GVL: graft-versus-leukemia; GVHD: graft-versus-host disease; HA: histocompatibility antigen; MST: median survival time; PEA: phycoerythrin/streptavidin; SPC: spleen cells; TCD: T cell depletion; WBC: white blood cells; WBI: whole body irradiation.

The present inventors have surprisingly found that treatment of mammals subjected to allogeneic bone marrow transplantation with interleukin-12, with or without co-administration of T-cell depleted syngeneic marrow, results in prolonged survival of said mammals, a result which indicates that interleukin-12 is useful for prevention of graft-versus-host disease in some cases and in amelioration of said disease in other cases. Specifically, as set forth in Example 1 below, mice which had been lethally irradiated and infused with bone marrow and spleen cells from fully MHC mismatched donor mice demonstrated prolonged survival from a course of interleukin-12 prophylaxis.

The present invention also demonstrates that IL-12 mediates distinct effects on GVHD- and GVL-associated T cell-mediated alloreactivity. In mice in which IL-12 mediated a significant protective effect against GVHD, marked GVL effects on allogeneic T cells against EL4 were observed. GVL effects depended on alloreactivity, as IL-12 did not induce protection in recipients of syngeneic (B 10) spleen cells. GVL effects against EL4 leukemia were CD8-dependent in IL-12-treated mice. Furthermore, applicants analyzed IL-12-treated recipients of EL4 cells and A/J spleen cells which survived for more than 100 days, and no EL4 cells were detected in bone marrow, spleen, thymus, liver, kidneys or peripheral blood cells by flow cytometry and/or tissue culture. Furthermore, no tumor-induced mortality was observed in lethally irradiated secondary B10 recipients of CD4 and CD8 cell-depleted spleen cells and marrow from these animals by 100 days of follow-up. Thus, EL4 cells were completely eradicated from IL-12-treated leukemic recipients which received allogeneic spleen cells. Applicants' previous data showed that IL-12 markedly increases IFN-γ production on days 2 and 3 post-BMT. The inhibitory effect on GVHD and the GVL effects against EL4 were diminished in IL-12 treated mice by neutralizing anti-IFN-γ mAb. Therefore, IL-12-mediated IFN-γ production plays a role in the protective effect of IL-12 against GVHD, and is involved in the GVL effect against EL4 leukemia in IL-12-treated mice. Thus, applicants have demonstrated that GVHD and GVL are separable functions of allogeneic T cells, and that protection from GVHD and leukemic relapse can be provided by a single molecule.

In accordance with the present invention, therefore, interleukin-12 is defined as a heterodimeric glycoprotein comprised of two covalently linked subunits, one of said subunits having a molecular weight of about 40 kD and being characterized by the amino acid sequence set forth in SEQ ID NO:1/SEQ ID NO:2, and the other subunit having a molecular weight of about 35 kD and being characterized by the amino acid sequence set forth in SEQ ID NO:3/SEQ ID NO:4. Any form of interleukin-12 may be used as a component of the pharmaceutical composition used to practice the method of the invention, so long as that form of interleukin-12 is capable of preventing, ameliorating, or treating graft-versus-host disease in a mammal at risk for that disease. For example, interleukin-12 may be in the form of the heterodimer comprised of a 40 kD subunit disulfide-bonded to a 35 kD subunit. When interleukin-12 is a heterodimer, the 40 kD subunit has substantial homology to the 40 kD subunit of human interleukin-12 as set forth in SEQ ID NO: 1/SEQ ID NO: 2 and is disulfide bonded to a 35 kD subunit having substantial homology to the 35 kD subunit of human interleukin-12 as set forth in SEQ ID NO:3/SEQ ID NO:4. "Substantial homology" means greater than 75% homology at the amino acid level, while retaining the ability to preventing, ameliorating, or treating graft-versus-host disease in a mammal at risk for that disease. Another form of interleukin-12 which may be used in the present invention is an interleukin-12 subunit capable of preventing, ameliorating, or treating graft-versus-host disease in a mammal at risk for that disease. Such an interleukin-12 40 kD subunit has substantial homology to the human interleukin-12 40 kD subunit of SEQ ID NO: 1/SEQ ID NO:2, and such an interleukin-12 35 kD subunit has substantial homology to the human interleukin-12 35 kD subunit of SEQ ID NO:3/SEQ ID NO:4. Fragments of the interleukin-12 subunits that retain interleukin-12 biological activity are also be useful to prevent or treat graft-versus-host disease in a mammal at risk for that disease, in accordance with the present invention.

For use in the present invention, it is preferable to produce interleukin-12 recombinantly, through expression of DNA sequences encoding one or both of the interleukin-12 subunits in a suitable transformed host cell. For example, using known methods the DNA sequences encoding human interleukin-12 set forth in SEQ ID NO: 1 (40 kD subunit) and SEQ ID NO:3 (35 kD subunit) may be linked to an expression vector such as pED (Kaufinan et al., Nucleic Acids Res. 19, 4484–4490 (1991)). In such an expression vector, sequences which optimize translation such as CCACC (Kozak, M., Nucleic Acids Res. 12, 857–871 (1984)) may be added 5' to the initiation codon using known methods. The expression vector containing the interleukin-12 subunits may then be transformed into a host cell, and protein expression may be induced and maximized, to produce heterodimeric human interleukin-12. For production of heterodimeric interleukin-12,the DNA sequences encoding the interleukin-12 subunits may be present on different expression plasmids or present in tandem on a single expression plasmid.

When a subunit or fragment of interleukin- 12 is used to practice the present invention, it may also be produced recombinantly using known methods. For example, the DNA sequence encoding the human interleukin-12 40 kD subunit set forth in SEQ ID NO: 1 may be linked to an expression vector, transformed into a host cell, and expression induced and maximized to produce the human interleukin-12 40 kD subunit. Similarly, the DNA sequences encoding the human interleukin-12 35 kD subunit as set forth in SEQ ID NO:3 may be linked to an expression vector, transformed into a host cell, and expression induced and maximized to produce the corresponding protein. Of course, degenerate DNA sequences encoding the interleukin-12 subunits may also be employed to produce interleukin-12 for use in the present invention, as can DNA sequences encoding allelic variants of the interleukin-12 subunits.

Any suitable expression vector may be employed to produce interleukin-12 for use in the present invention. For mammalian expression, numerous expression vectors are known in addition to the pED vector mentioned above, such as pEF-BOS (Mizushima et al., Nucleic Acids Res. 18, 5322 (1990)); pXM, pJL3 and pJL4 (Gough et al., EMBO J. 4, 645–653 (1985)); and pMT2 (derived from pMT2-VWF, A.T.C.C. #67122; see PCT/US87/00033). Suitable expression vectors for use in yeast, insect, and bacterial cells are also known. Construction and use of such expression vectors is well within the level of skill in the art.

Suitable host cells for recombinant production of interleukin-12 useful in the present invention include, for example, mammalian cells such as Chinese hamster ovary (CHO) cells, monkey COS cells, mouse 3T3 cells, mouse L cells, myeloma cells such as NSO (Galfre and Milstein, Methods in Enzymology 73, 3-46 (1981)), baby hamster kidney cells, and the like. Interleukin-12 may also be produced by transformation of yeast, insect, and bacterial cells with DNA sequences encoding the interleukin-12 subunits, induction and amplification of protein expression, using known methods.

Recombinantly produced interleukin-12 can be purified from culture medium or cell extracts by conventional purification techniques. Culture medium or cell extracts containing interleukin-12 may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylamioethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. The purification of interleukin-12 from culture supernatant may also include one or more column steps over such affinity resins as lectin-agarose, heparin-toyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify interleukin-12 for use in the present methods and compositions. Some or all of the foregoing purification steps, in various combinations, can be employed to provide a substantially homogeneous isolated recombinant protein. Purification of interleukin-12 subunits or fragments for use in the present invention may differ from the optimal protocol for purification of the heterodimeric protein.

Preferably, when human interleukin-12 is produced recombinantly as set forth above, it may be purified by the following method. The cells in which the human interleukin-12 has been made may be removed from the conditioned medium by filtration, and the conditioned medium is loaded onto Q-Sepharose FastFlow™ (available from Pharmacia) or an equivalent anion exchange medium, which has been equilibrated in 10–30 mM Tris-HCl, pH 7.8–8.3. The column is then washed extensively with the same buffer followed by a wash with 30–45 mM histidine, pH 5.1–5.8, followed by a wash with the original equilibration buffer. The recombinant human interleukin-12 is eluted from the column with a buffer containing 20–50 mM Tris-Hcl, pH 7.8–8.5, and 0.15 to 0.50M NaCl. the eluted material is loaded onto CM-Sepharose FastFlow1υ (available from Pharmacia) or equivalent cation exchange medium which has been equilibrated in 20–50 mM MES, pH 5.7–6.4, and washed extensively with the same buffer. The column is washed with a buffer containing 20–40 mM sodium phosphate, pH 6.8–7.5 and 0.2–0.5 M NaCl. The eluted material is concentrated using an Amicon™ S1Y30 or equivalent spiral cartridge membrane which has been washed and equilibrated in the elution buffer used in the CM-Seplarose FastFlow™ column. The material is concentrated to approximately 5% of the column volume of the final chromatographic step, which is size exclusion using S200 Sephacryl™ (available from Pharmacia) or an equivalent size exclusion resin. The size exclusion column is equilibrated and eluted with phosphate buffered saline, pH 7.2–7, and the recombinant human interleukin-12 peak is collected and filtered for use in the method of the invention. Those of skill in the art of protein purification may use alternative purification methods to obtain recombinantly-produced human interleukin-12 for use in the method of the invention.

Interleukin-12 may be purified from culture medium or extracts of cells which naturally produce the protein and used in the present invention. Exemplary purification schemes for naturally produced interleukin-12 are set forth in PCT/US91/06332 and in EP 433827.

For use in the method of the invention, a therapeutically effective amount of interleukin-12 is administered to a mammal at risk of developing graft-versus-host disease. As used herein, the term therapeutically effective amount means the total amount of each active component of the pharmaceutical composition or method that is sufficient to show a meaningful patient benefit, i.e., a reduction in the incidence or severity of acute or chronic graft-versus-host disease compared to that expected for a comparable group of patients not receiving interleukin-12, as determined by the attending physician. When applied to an individual active ingredient administered alone, the term refers to that ingredient alone. When applied to a combination, the term refers to combined amounts of the active ingredients that result in the therapeutic effect, whether administered in combination, serially, or simultaneously.

In practicing the method of the present invention, a therapeutically effective amount of interleukin-12 is administered to a mammal at risk of developing graft-versus-host disease. The interleukin-12 may be administered in accordance with the method of the invention either alone or in combination with other therapies such as treatments employing T cell-depleted autologous or syngeneic bone marrow, immunosuppressive drugs, cytokines, lymphokines, or other hematopoietic factors.

When co-administered with T-cell-depleted autologous or syngeneic bone marrow, immunosuppressive drugs, one or more cytokines, lymphokines, or other hematopoietic factors, the interleukin-12 may be administered either simultaneously with the T-cell-depleted autologous or syngeneic bone marrow, immunosuppressive drugs, cytokine(s), lymphokine(s), other hematopoietic factor(s), or sequentially. If administered sequentially, the attending physician will decide on the appropriate sequence of administering the interleukin-12 in combination with the T-cell depleted autologous or syngeneic bone marrow, immunosuppressive drugs, cytokine(s), lymphokine(s), and other hematopoietic factor(s).

Administration of the interleukin-12 used to practice the method of the present invention can be carried out in a variety of conventional ways, such as oral ingestion, inhalation, or cutaneous, subcutaneous, or intravenous injection. Intravenous or subcutaneous administration to the patient is preferred.

When a therapeutically effective amount of interleukin-12 is administered orally, the interleukin-12 will be in the form of a tablet, capsule, powder, solution or elixir. When administered in tablet form, the pharmaceutical composition of the invention may additionally contain a solid carrier such as a gelatin or an adjuvant. The tablet, capsule and powder contain from about five to 95% interleukin-12, preferably from about 25–90% interleukin-12. When administered in liquid form, a liquid carrier such as water, petroleum, oils of animal or plant origins such as peanut oil, mineral oil, soy bean oil, or sesame oil, or synthetic oils, may be added. The liquid form of the pharmaceutical composition may further contain physiological saline solution, dextrose, or other saccharide solutions, or glycols such as ethylene glycol, propylene glycol or polyethylene glycol. When administered in liquid form, the pharmaceutical composition contains about 0.5 to 90% by weight of interleukin-12 and preferably from about 1 to 50% interleukin-12.

When a therapeutically effective amount of interleukin-12 is administered by intravenous, cutaneous or subcutaneous injection, the interleukin-12 will be in the form a pyrogen-free, parenterally-acceptable aqueous solution. The preparation of such parenterally-acceptable protein solutions, having due regard to pH, isotonicity, stability, and the like, is within the skill in the art. A preferred pharmaceutical composition for intravenous, cutaneous, or subcutaneous injection should contain, in addition to interleukin-12, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition for use in the present method may also contain stabilizers, preservatives, buffers, antioxidants, or other additive known to those with skill in the art. It is contemplated that the pharmaceutical composition used to practice the method of the present invention should contain about 0.1 pg to about 100 mg of interleukin-12 per ml of solution, preferably about 0.1 mg of interleukin-12 per ml of solution.

In practicing the method of preventing or ameliorating graft-versus-host disease in accordance with the present invention, it is contemplated that the duration of the application of interleukin-12 will be in the range of 12–48 hours of continuous or intermittent subcutaneous or intravenous administration, beginning at the time of transplantation. For the purpose of the present invention, "at the time of bone marrow transplantation" is defined as being during the 1 hour period before or the 1 to 24 hour period after the bone marrow transplantation. As an example of a method for preventing or ameliorating graft-versus-host disease, preferably 1 µg/kg to 100 µg/kg of interleukin-12 may be administered daily to the mammal, more preferably 5 ng/kg to 10 µg/kg of interleukin-12 may be administered daily to the mammal, and most preferably 10 ng/kg to 1 jg/kg may be administered daily to the mammal. In one preferred dosage regimen, the first dose of interleukin-12 is given one hour after bone marrow transplantation and two more doses are given on days one and two post-transplant. Alternative treatment regimens may be appropriate for individual patients and will be determined by the attending physician, taking into account the nature and severity of the condition being treated, and the nature of the prior treatments which the patient has undergone.

Modifications of the treatment regimen set forth above for prevention or ameliorating graft-versus-host disease may be made for treatment of ongoing acute or chronic graft-versus-host disease. For the purpose of the present invention, "acute graft-versus-host disease" is defined as occurring during the time period from three days to 100 days post transplantation in humans or from three days to 30 days post transplantation in mice; and "chronic graft-versus-host disease" is defined as occurring at any time after 100 days post-transplantation in humans or at any time after 30 days post transplantation in mice. As an example of a method for treating ongoing acute or chronic graft-versus-host disease, 1 pg/kg to 100 µg/kg may be administered daily to a mammal experiencing acute or chronic graft-versus-host disease, until improvement or remission of the symptoms of acute or chronic graft-versus-host disease is observed. Ultimately, the attending physician will decide on the appropriate duration of subcutaneous or intravenous therapy using the pharmaceutical composition of interleukin-12 in the method of the present invention.

EXAMPLE 1

Use of Recombinant murine IL-12 for the Inhibition of Graft-Versus-Host Disease (GVHD) in Mice Thirty C57Bl/10 mice were lethally irradiated with 10.25 Gy whole body irradiation. On the same day, 27 of these mice received an intravenous inoculum containing $9 \times 10^6$ bone marrow cells and $13 \times 10^6$ spleen cells (as an additional source of GVHD-causing T lymphocytes) from fully MHC-mismatched (and multiple minor histocompatibility antigen-mismatched) A/J donor mice. In addition, 18 of these mice received $5 \times 10^6$ B10 (i.e., host-type syngeneic, the murine counterpart of autologous marrow) T cell-depleted (TCD) bone marrow cells in the same inoculum. The three remaining mice served as non-GVHD controls, and received T cell-depleted B10 marrow only.

Nine of the 18 mice receiving A/J bone marrow and spleen cells plus TCD B10 BMC were treated with recombinant murine interleukin-12 (Schoenhaut et al., J. Immunol. 148, 3433–3440 (1992)) at a dose of 1 µg (approximately 50 µg/kg) per day intraperitoneally on days 0, 1, and 2 (day 0 being the day of the transplant). In addition, the group receiving A/J bone marrow and spleen cells alone also received a similar course of interleukin-12 prophylaxis.

The result of this experiment was that most of the mice (8 of 9) receiving A/J bone marrow and spleen cells plus TCD B10 bone marrow cells died by day 10. The death was due to GVHD, as recipients of TCD syngeneic marrow alone all survived in excellent health. In the interleukin-12-treated group that also received A/J bone marrow and spleen cells plus TCD B10 bone marrow cells, none of the nine animals died by day 10, and all were still alive by day 20. This protective effect of interleukin-12 was somewhat dependent on the co-administration of TCD B10 bone marrow cells, since 5 of 9 animals receiving A/J bone marrow and spleen cells without TCD B10 BMC, plus interleukin-12 treatment, died by day 9. Thus, interleukin-12 protected against acute GVHD mortality, and this effect was most marked when TCD host-type bone marrow cells were also given. In a second experiment, animals receiving interleukin-12 prophylaxis against graft-versus-host disease induced by A/J bone marrow and spleen cells showed similar graft-versus-host disease protection, both in the presence and in the absence of T-cell-depleted host-type bone marrow.

EXAMPLE 2

Maintenance of GVL Effects

Since IL-12 is not globally immunosuppressive and might even have anti-leukemic activity of its own, applicants have examined the possibility that IL-12 could preserve GVL effects of donor T cells in the EL4 leukemia/lymphoma model, while GVHD is inhibited. Applicants' results indicate that IL-12 separates the GVHD- and GVL-promoting activities of allogeneic T cells. Marked GVL effects were observed in mice in which IL-12 mediated a significant protective effect against GVHD. Applicants also analyzed the contributions of IFN-γ and allogeneic T-cell subsets to GVL effects in IL-12-treated leukemic recipients.

MATERIALS AND METHODS

Mice. Specific pathogen-free female C57BL/10SnCR (B10, H-$2^b$, $K^bI^bD^b$) and A/J (H-2a, $K^aI^aD^d$) mice were obtained from the Frederick Cancer Research Facility (NIH, Bethesda, Md.) Animals were housed in sterilized microisolator cages and received autoclaved feed and autoclaved, acidified drinking water.

Whole body irradiation (WBI) and BMT. Recipient mice were lethally irradiated (10.25 Gy, $^{137}$CS source, 1.1 Gy/min) and reconstituted within 4 to 8 hours by a single 1 ml intravenous inoculum containing $5\times10^6$ B 10 T cell-depleted (TCD) BMC plus $10\times10^6$ A/J BMC and $15\text{-}18\times10^6$ A/J spleen cells, or by $5\times10^6$ TCD B10 BMC with or without $15\text{-}18\times10^6$ B10 spleen cells (syngeneic control group). TCD B10 BMC was used because it enhances the IL-12-mediated inhibition of GVHD, even though the host-type cells are eliminated within one week after BMT (Sykes et al., Blood 86:2429,1995). Host-type (B10) BMC and, in some experiments, allogeneic BMC and spleen cells, were depleted of T cells (TCD), or of CD4$^+$ or CD8$^+$ cells with anti-CD4 mAb (GK1.5 ascites) (Dianlynas et al., J. Immunol. 131:2445, 1983) and/or anti-CD8 mAb (2.43 ascites) (Sarmiento et al., J. Immunol. 125:2665, 1980) plus low toxicity rabbit complement (1:14 dilution), as previously described (Sykes et al., J. Immunol. 150:197, 1993). T cell depletion was analyzed by flow cytometry using indirect staining as described (Sykes et al., Cel., Immunol. 127:260, 1990). In adoptive BMT, secondary recipients (B10) were lethally irradiated and reconstituted with CD4 and CD8-depleted BMC and spleen cells prepared from long-term (more than 100 days) surviving non-leukemic (as control) and leukemic recipients of allogeneic BMT. These secondary recipients also received $5\times10^6$ fresh TCD B10 BMC. To avoid bias from cage-related effects, animals were randomized before and after BMT as described (Sykes et al., J. Exp. Med. 171:645, 1990). Survival was followed for 100 days.

IL-12 Administration. Murine recombinant IL-12, with specific activity of 4.9 to $5.5\times10^6$ U/mg, was injected intraperitoneally into recipient mice (4,900 IU/mouse) in a single injection approximately one hour prior to BMT.

EL4 Leukemia Experiments. The EL4 leukemia model we have previously described (Sykes et al., Proc. Natl. Acad. Sci. USA 87:5633, 1990; Sykes et al., Bone Marrow Transplant. 4:465, 1989) was employed. E14F cells (referred to here as EL4), a subline of the B6 T cell leukemia/lymphoma EL4, were thawed from frozen vials and maintained in culture for 4 to 14 days before each experiment, and 500 cells were administered on day 0 along with BMC and spleen cells in a single 1 ml i.v. injection. Carcasses were saved in formalin after death or euthanasia, and in some leukemic and non-leukemic mice, the spleen, liver, kidney and lung were embedded in paraffin, sectioned and stained with hematoxylin and eosin. Necropsies and histologic analysis were performed on randomly chosen samples. The presence of tumor at death was determined by gross autopsy and/or histological observation by an observer who was unaware of which treatment group the carcasses belonged to, as previously described (Sykes et al. Bone Marrow Transplant. 4:465, 1989).

Flow cytometric (FCM) analysis. FCM analysis of peripheral white blood cells (WBC) was performed on a FACScan (Becton Dickinson, Mountain View, Calif.). WBC were prepared by hypotonic shock, as described (Tomita et al., Blood 83:939, 1994). Cells were stained with biotinylated anti-H-$2D^d$ mAb 34-2-12 (Ozato et al., Transplantation 34:113, 1982), FITC-labeled rat anti-mouse CD4 mAb GK1.5 (Dialynas et al., J. Immunol. 131:2445, 1983) and rat anti-mouse CD8 mAb 2.43 (Sarmiento et al., J. Immunol. 125:2665, 1980) or FITC-labeled Thy 1.2 for 30 min at 4° C., then washed and incubated for 15 minutes at 4° C. with phycoerythrin/streptavidin (PEA). In order to block non-specific FcγR binding of labeled antibodies, 10 μl of undiluted culture supernatant of 2.4G2 (rat anti-mouse FcγR mAb) (Unkeless, J. Exp. Med. 150:580, 1979) was added to the first incubation. Mouse IgG2a mAb HOPC-1 was used as a non-staining negative control antibody. Dead cells were excluded by gating out low forward scatter/high propidium iodide-retaining cells.

Anti-IFN-γmAb administration. Rat IgG1 anti-mouse interferon-γ mAb R4-6A2 (Spitalny et al., J. Exp. Med. 159:1560, 1984) was ammonium sulfate precipitated from ascites prepared in BALB/C nude mice. Antibody content was quantified using rat $IgG_1$-specific inhibition ELISA. A single injection of 2.5, 5 or 10 mg of R4-6A2 was administered on day 1 with respect to BMT.

Statistical analysis. Survival data were analyzed using the Kaplan-Meier method of life table analysis, and statistical analysis was performed with the Mantel-Haenzsen test. A P value of less than 0.05 was considered to be significant.

Results

Figure 1:
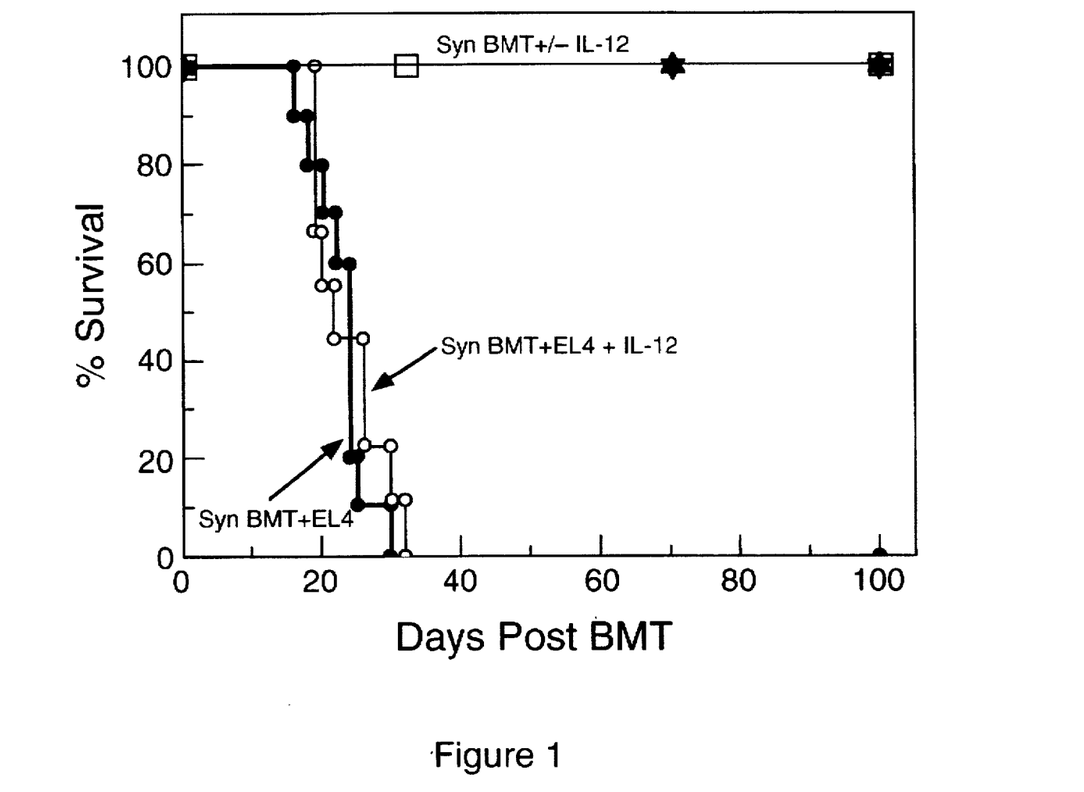
FIG. 1. Syngeneic spleen cells no not mediate an anti-leukemia effect in IL-12 treated mice. Results of two experiments that gave similar results are combined. B10 mice were treated with 10.25 Gy WBI and received $5 \times 10^6$ TCD B10 BMC, 15 or $18 \times 10^6$ B10 spleen cells plus 500 El4 cells with no further treatment (●; n=10) or with 4,900 IU EL-12 intraperitoneally on day 0 (○;n=9). Non-leukemic control mice received similar inocula without EL4 cells with no further treatment (□; n=6) or with 4,900 IU intraperitoneally (★; n=6).

Syngeneic spleen cells do not mediate anti-tumor activity in IL-12-treated mice. The EL4 H-$2^b$ leukemia administered as recently described is highly lethal, and as few as 100 cells are sufficient to kill lethally irradiated, syngeneically reconstituted H-$2^b$ mice. Since IL-12 has been shown to promote anti-tumor immunity, applicants first investigated whether or not IL-12 could mediate anti-leukemia effects of its own, by promotion of host immunity. Applicants compared tumor-induced mortality in control and IL-12-treated B10 mice after syngeneic BMT. B10 mice were lethally irradiated, and injected with 500 EL4 cells along with $5\times10^6$ TCD B10 BMC and $15\times10^6$ B10 spleen cells. As shown in FIG. 1, a single dose of 4,900 IU of IL-12 had no effect on tumor-induced mortality. In both the control (Syn BMT+EL4) and the IL-12-treated (Syn BMT+EL4+IL-12) group, almost all mice were dead by 30 days post transplantation, and marked enlargement of the spleen and/or kidney was observed in 18 of 19 carcasses at autopsy.

Figure 2:
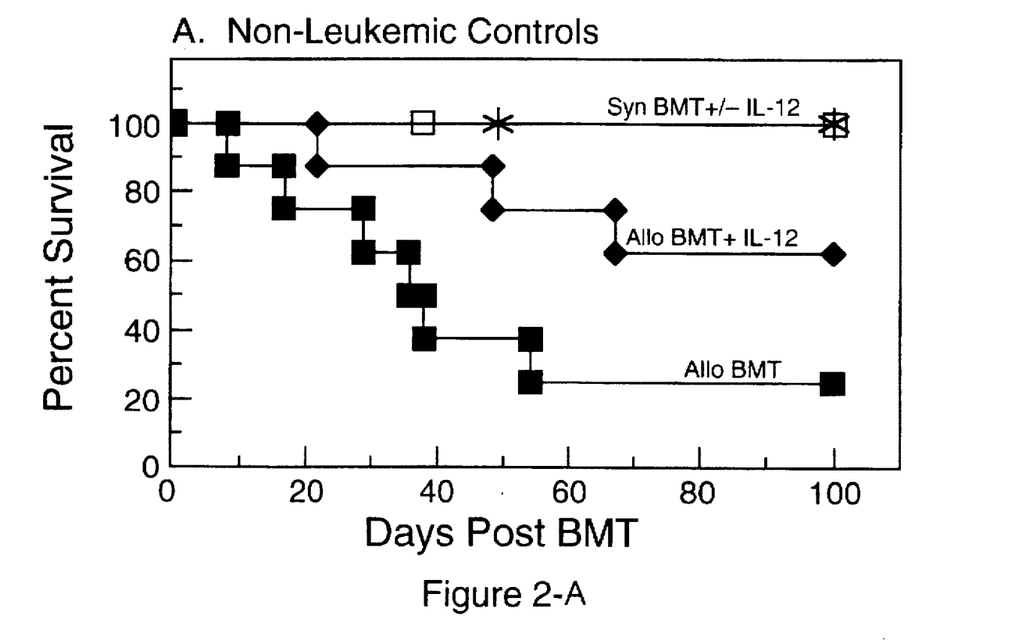
FIG. 2A and 2B. Preservation of allogeneic GVL effects in IL-12 treated mice. B 10 (H-$2^b$) mice were lethally irradiated on day 0.

Preservation of allogeneic GVL effects in IL-12-treated mice. Applicants next evaluation whether or not allogeneic GVL effects could be preserved while GVHD is inhibited by IL-12 in the EL4 leukemia model (Sykes et al., J. Immunol. 150:197, 1993). Lethally irradiated B10 mice received a mixture of $5 \times 10^6$ syngeneic (B10) TCD BMC, fully MHC plus multiple minor antigen-mismatched A/J BMC ($10 \times 10^6$) and A/J spleen cells ($15-18 \times 10^6$), plus 500 EL4 cells. A syngeneic control group received the same number of B10 TCD BMC and spleen cells. The results are shown in FIG. 2. In non-leukemic recipients, a marked protective effect against GVHD was observed in EL-12-treated animals. GVHD mortality was clearly inhibited in IL-12-treated mice (Allo BMT+IL-12) when compared to untreated controls which received similar inocula (Allo BMT) (p<0.01) (FIG. 2A). A similar level of protection from GVHD was also observed in IL-12-treated leukemic recipients (FIG. 2B). In addition, administration of EL4 did not result in a detectable increase in mortality in these mice, as survival curves were similar in groups receiving (Allo BMT+E4+IL-12) or not receiving (Allo BMT+IL-12) EL4 (FIGS. 2A and 2B). Allogeneic cells were necessary for an anti-leukemic effect in IL-12-treated mice, as IL-12 treatment did not result in a detectable GVL effect in syngeneic controls in the same experiment (FIG. 2B). Therefore, the GVL effect of allogeneic spleen cells was preserved while allogeneic spleen cell-mediated GVHD was inhibited by IL-12. Similar results were obtained in three of three separate similar experiments (Table 1). In Experiment 1, although the median survival time (MST) of the IL- 12 treated GVHD group (Group 3) was delayed by only 8 days compared to the GVHD control group (Group 2), acute GVHD was clearly inhibited by IL-12, as the mortality in IL-12 treated group was only $\frac{1}{3}$ of that in IL-12-untreated control group by 30 days post BMT. In Experiments 2 and 3, MST's readily reflected the GVHD protection conferred by IL-12 treatment. Autopsy analysis was performed in randomly selected carcasses without knowledge of which treatment the animals had received. As shown in Table 1, gross evidence for tumor, which was detected in almost all EL4 recipients of B 10 TCD BMC and spleen cells, was not found in IL-12-treated EL4 recipients of B10 TCD BMC plus A/J BMC and spleen cells. Leukemic infiltration of kidneys, liver, spleen or lung was readily apparent in the syngeneic BMT controls receiving EL4 (Table 1, Groups 4 and 5 in Experiment 1), but was not detected in IL-12-protected recipients of allogeneic cells (Table 1, Group 6 in Experiment 1) by histologic analysis. It was impossible to detect a GVL effect of allogeneic spleen cells in EL4 recipients not receiving IL- 12, as most mice died of acute GVHD before EL4-induced death began in syngeneic control mice (Table 1, Experiment 3).

EL4 cells were eradicated from IL-12-treated recipients of allogeneic spleen cells.

Inhibition of leukemic mortality in IL-12-treated EL4 recipients which received B10 TCD BMC plus A/j BMC and spleen cells suggested that leukemic growth was inhibited. We next evaluated whether or not EL4 cells were completely eradicated by allogeneic cell-mediated GVL effects in these animals. BMC, thymocytes, spleen cells, peripheral blood cells and tissue fractions of liver and kidney were prepared from long-term surviving IL-12-treated EL4 recipients (9 mice from Group 6 in Experiments 1 and 2; Table 1) when sacrificing them after 100 days of follow-up. These cells were cultured in vitro for one month, and no EL4 cells grew in the cultures. Thymocytes, spleen cells, BMC and peripheral white blood cells from these animals were also analyzed by two-color FACS. Since T cells in long-term surviving IL-12-treated recipients are of donor-type (A/J, $H-2D_d$) (Illdstad et al., J. Immunol. 136:28, 1986; Sykes et al., J. Immunol. 141:2282, 1988), and EL4 cells are $H-2D^2$ mAb plus PEA. No ELM cells with the $H-2D^d$, Thy1.2+ phenotype were detected, as all Thy1.2+ cells were donor-type ($H-2D^{d+}$) in both non-leukemic and leukemic recipients of allogeneic BMT (data not shown).

Figure 3:
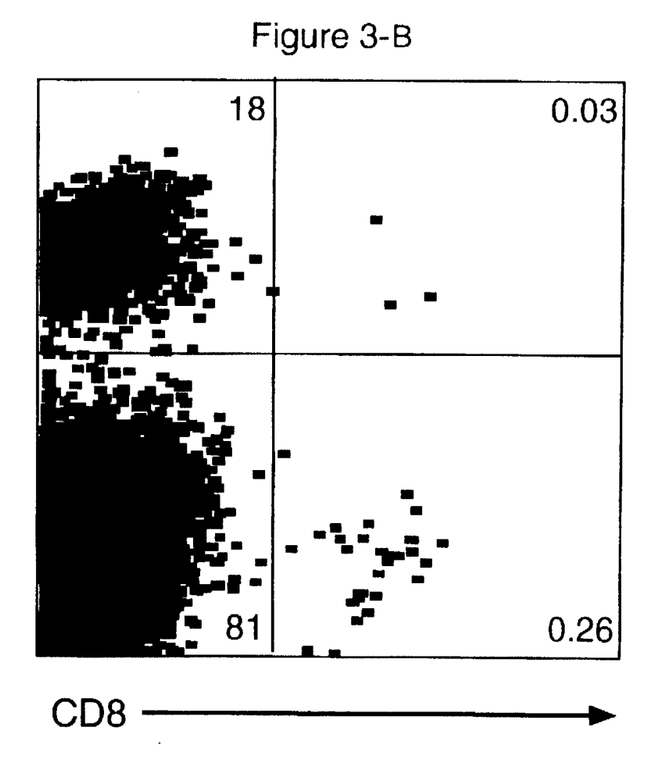

To further test for residual leukemic cells in IL-12-protected recipients of EL4 and allogeneic cells, we transferred TCD BMC and TCD spleen cells from these long-term (more than 100 days) surviving IL 12-treated EL4 recipients (9 mice from Group 6 in Experiments 1 and 2; Table 1) and non-leukemic recipients (as controls) (5 mice from Group 3 in Experiment 2; Table 1), along with TCD B10 BMC, into lethally irradiated secondary B10 recipients (one to two transfer). The spleen is a major site of leukemia infiltration in this EL4 model (25). Potentially GVH-reactive A/J CD4 and CD8 T cells were eliminated from inocula, in order to allow any residual EL4 cells the best opportunity to grow in secondary host-type recipients. Mixed chimerism was observed in these secondary recipients by flow cytometric analysis (FIG. 3), indicating that GVH-reactive T cells were completely depleted from the spleens and marrow of the donor chimeras (Singer et al., J. Exp. Med. 153:1286, 1981; Ildstad et al., J. Exp. Med. 162:231, 1985; Ildstad et al., Nature 307(5947):168, 1985). However, no leukemia-induced mortality was observed by 100 days of follow-up, and no gross evidence for tumor was detected by autopsy in any of 18 mice sacrificed 100 days following transfer. These results suggest that EL4 leukemic cells had been completely eradicated from IL-12-treated allogeneic BMT recipients.

Figure 4:
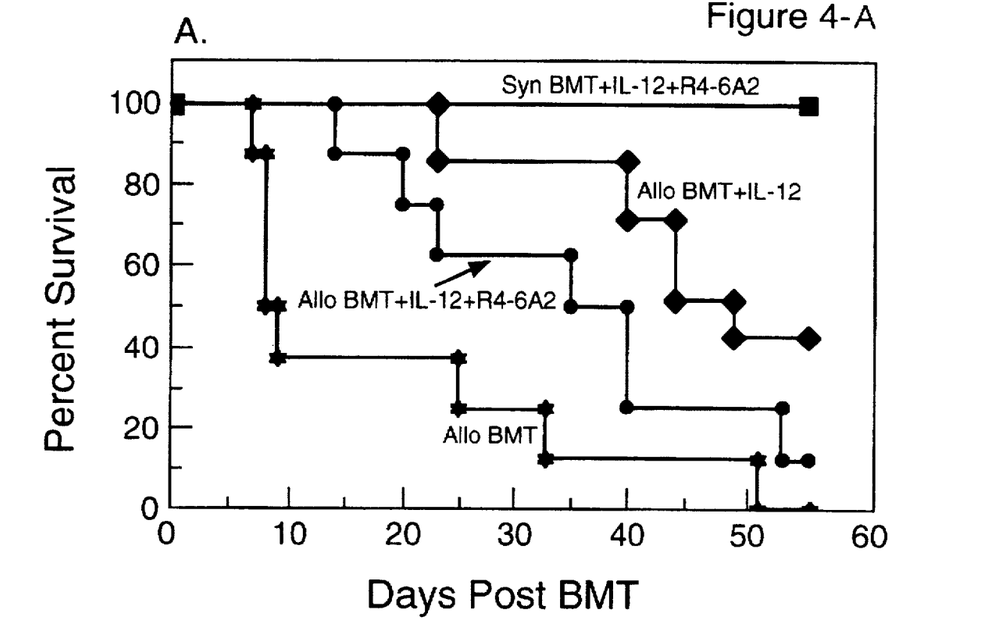

Role of IFN-γ in IL-12-mediated GVHD protection. Our previous results showed that IL-12 treatment markedly increases serum IFN-γ levels on days 2 and 3 post-BMT, and that the later, GVHD-associated rise in serum IFN-γ on day 4 is markedly inhibited (Sykes et al., Blood 86:2429, 1995; Szebeni et al., Transplantation 580:1385, 1994). We therefore investigated the role of IL-12-induced IFN-γ production in the inhibitory effect against GVHD and in GVL effects of allogeneic spleen cells in IL-12-treated mice. On day 1 post-BMT, we injected 2.5 mg of R4-6A2, a neutralizing rat-anti-mouse IFN-γ mAb (Spitalny et al., J. Exp. Med. 159:1560, 1984) into IL-12-treated B10 mice which received $5 \times 10^6$ B10 TCD BMC plus $10 \times 10^6$ A/J BMC and $15 \times 10^6$ A/J spleen cells. Although GVHD-induced mortality was slightly delayed by R4-6A2 (Allo BMT+R4+6A2) compared to GVHD controls which received similar BMT inocula without R4-6A2 (Allo BMT), the delay did not achieve statistical significance (FIG. 4). As usual, IL-12 treatment induced a significant delay in GVHD mortality (Allo BMT+IL-12) compared to GVHD controls (Allo BMT) (p<0.005). This delay was markedly inhibited by R4-6A2 (allo BMT+L-12+R4-6A2) (p<0.005) (FIG. 4), so that the time of mortality in the group receiving IL-12 and R4-6A2 (Allo BMT+L-12+R4-6A2) was similar to that of the group treated with R4-6A2 (2.5, 5, or 10 mg per mouse), and similar results were observed (data not shown).

Role of IFN-γ in GVL effects of allogeneic cells in IL-12-treated mice.

We next investigated the possible role of IFN-γ in the GVL effects of allogeneic spleen cells in L-12-treated mice. As shown in Table 2, IL-12-treated EL4 recipients of TCD B10 BMC plus A/J BMC and spleen cells (Allo BMT, IL-12, EL4) were significantly protected from both GVHD- and leukemia-induced mortality when compared to GVHD control recipients of similar inocula without IL-12 (Allo BMT) (p<0.01), and syngeneic leukemic recipients of B10 TCD BMC and EL4 cells (Syn BMT, EL4) (p<0.01), and syngeneic leukemic recipients of B10 TCD BMC and EL4 cells (Syn BMT, EL4) (p<0.01), respectively. The GVL effect of allogeneic cells was significantly reduced by injecting R4-6A2 on day one post-BMT. A significant acceleration in mortality (p<0.05) was detected in R4-6A2-treated, IL-12-treated EL4 recipients (Allo BMT, IL-12, R4-6A2, EL4) compared to IL-12-treated leukemic allogeneic BMT controls (Allo BMT, IL-12, EL4). Since R4-6A2 diminished the protective effect of IL-12 against GVHD in non-leukemic allogeneic BMT mice (FIG. 4 and Tabled 2), this acceleration of mortality in EL4 recipients could reflect a loss of GVHD protection, a loss of GVL effects, or both. However, autopsy and histological analysis indicated that the GVL effect in IL-12-treated mice was partially impaired by R4-6A2 treatment, as gross evidence of leukemia, similar to that observed in syngeneic EL4 controls (Syn BMT, EL4) was detected in 4/9 of these animals (Allo BMT, IL-12, R4-6A2, EL4) (Table 2), and leukemic infiltration of liver, kidney, or lung was observed in three of the five remaining mice. In contrast, no evidence for leukemia was detected at autopsy of IL-12-protected recipients of similar inocula without R4-6A2 (Allo BMT, IL-12, EL4) (Table 2), and no leukemic infiltration of liver, kidney or lung was observed by histological analysis. Adoptive BMT to test for residual leukemic cells was performed at day 64 post-BMT, by transferring CD4 and CD8-depleted BMC and spleen cells from IL-12-protected recipients of EL4 and allogeneic cells (5 mice in Group "Allo BMT, IL-12, EL4", Table 2), along with TCD host-type BMC into lethally irradiated, secondary recipients by 100 days of follow-up, and no gross evidence for leukemia was detected at autopsy when these mice were sacrificed. Together, our results suggest that IFN-γ is involved in the protective effect of IL-12 against acute GVHD, and is also involved in the GVL effect of allogeneic cells against EL4 leukemia in IL-12 treated mice.

Figure 5:
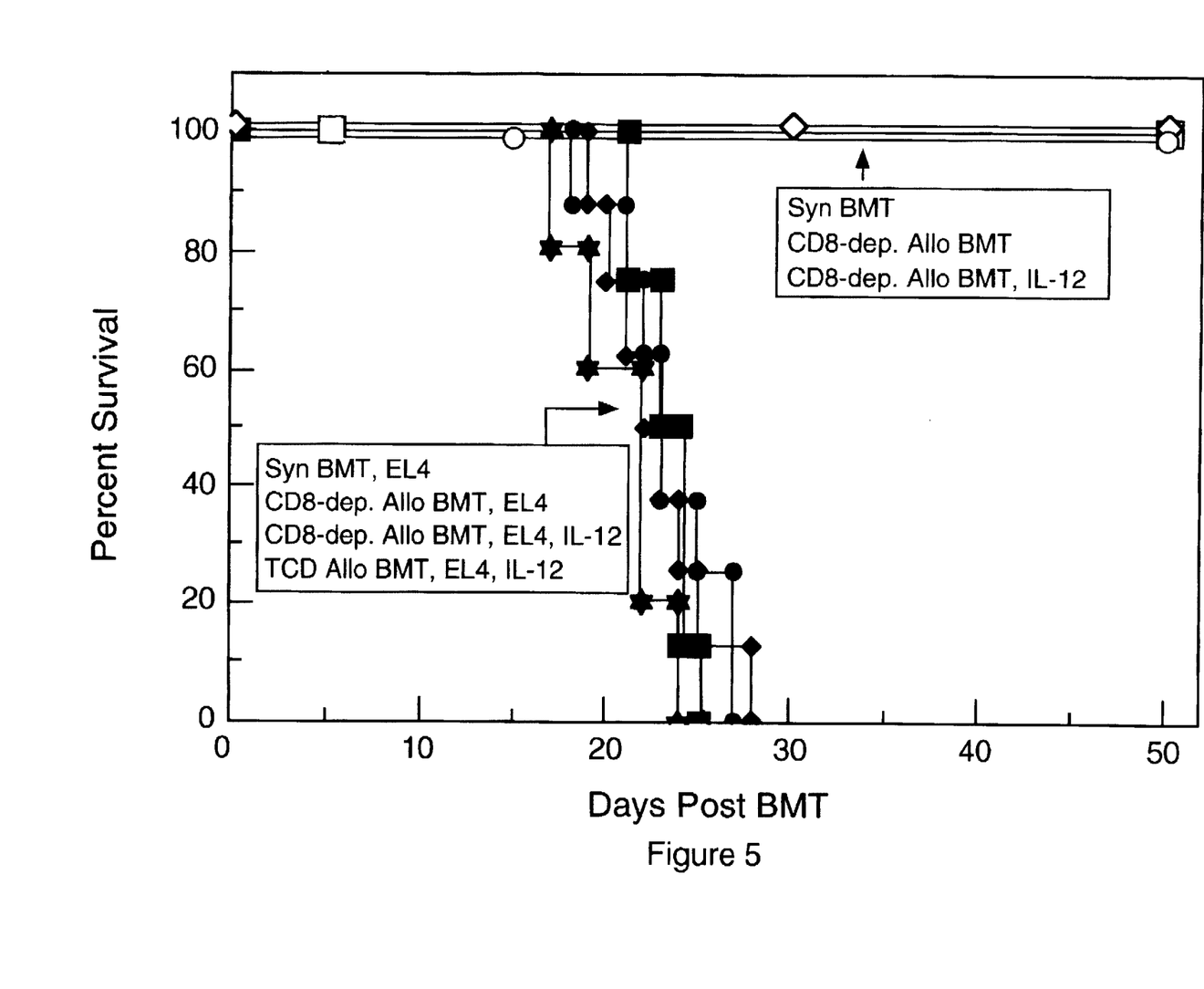
FIG. 5. GVL effect on allogeneic inocula against EL4 is CD8-dependent in both IL-12 treated and untreated EL4 recipients. Lethally irradiated B10 mice received TCD B10

Role of T cell subsets in GVL effects in IL12 treated mice. Since GVL effects against EL4 leukemia in the model used in this study were CD8-dependent and CD4-independent in untreated recipients of allogeneic BMC and spleen cells (Sykes et al., J. Immunol. 150:197, 1993), we next evaluated the contribution of donor T-cell subsets to GVL effects in IL-12-treated EL4 recipients. Lethally irradiated B10 mice received 5×10⁶ TCD B 10 BMC alone, or with 10×10⁶ TCD A/J BMC plus 10×106 CD8-depleted or 15×10⁶ TCD A/J spleen cells. Leukemic mice received similar inocula plus 500 EL4 cells. Since a reduced number of CD8-depleted A/J spleen cells was given in this experiment, no GVHD-induced early mortality was observed by 50 days in recipients of CD8-depleted A/J spleen cells (FIG. 5), although clinical manifestations of acute GVHD were observed. Tumor-related mortality in both IL-12-treated animals that received TCD A/J spleen cells or TCD B10 BMC (FIG. 5). In addition, gross evidence for leukemia was detected in all EL4 recipients by autopsy (data not shown). Similar rates of EL4-induced mortality were observed in IL-12-treated and untreated recipients of CD4- plus CD8-depleted A/J spleen cells (FIG. 5), suggested that CD8-independent NK cells were not directly involved in allogeneic spleen cell-mediated GVL effects.

Figure 6:
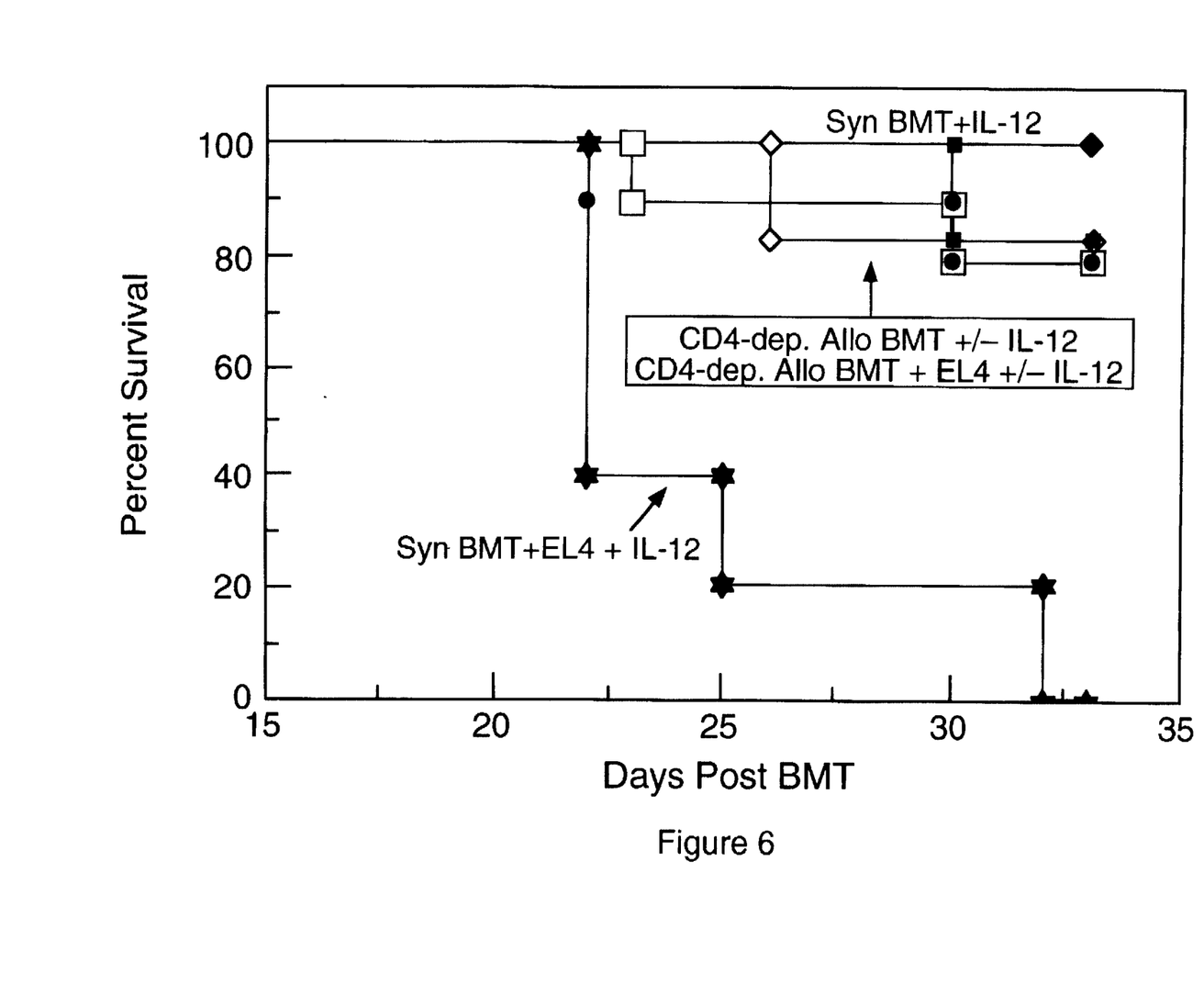
FIG. 6. Allogeneic cells mediate significant GVL effects against EL4 in the absence of CD4⁺ cells in both IL-12 treated and untreated EL4 recipients. B10 mice were treated with 10.25 Gy WBI, and received B10 TCD BMC plus A/J TCD BMC and A/JCD4-depleted spleen cells with our without IL-12 (CD4-dep. Allo BMT +/- IL-12) (◊; n=6/■; n=6). Leukemic recipients received similar inocula plus EL4 cells (CD4-dep. Allo BMT+EL4+/-IL-12) (●; n=10/□; n=1 leukemic and leukemic syngeneic controls which received B10 TCD BMC (Syn BMT+IL-12) (♦; n=3) and T10 TCD BMC plus EL4 (Syn BMT+EL4+IL-12) (★; n=5), respectively, were treated with IL-12.

In contrast to these results, a significant GVL effect against EL4 leukemia was observed in IL-12-treated EL4 recipients that received CD4-depleted A/j spleen cells (FIG. 6). Almost all mice in groups that received CD4-depleted A/J spleen cells plus EL4 cells survived longer than syngeneic leukemic controls (FIG. 6). Gross evidence for leukemia was detected in 10 of 10 EL4 recipients of B10 TCD BMC, but was only observed in one of 19 mice receiving CD4-depleted A/J spleen cells-plus EL4 cells (all mice were pooled from two similar experiments) by autopsy. Furthermore, the mortality in groups receiving CD4-depleted A/J spleen cells plus EL4 was similar to that in non-leukemic mice which received similar BMT inocula without EL4, indicating that EL4-induced mortality was inhibited by giving CD4-depleted A/J spleen cells. As $CD^{4+}$ cells are required for inducing acute GVHD in this model (Sykes et al., J. Immunol. 150:197, 1993), no mice died of acute GVHD in either EL-12-treated or untreated non-leukemic recipients of allogeneic cells in this experiment (FIG. 6).

Similar results were observed in the repeat experiment in which GVL effects were only observed in IL-12-treated recipients of non-CD8-depleted A/J spleen cells. Since almost all early deaths are caused by acute GVHD in this model, we summarized autopsy results of mice that died beyond 12 days after BMT in this experiment (Table 3). Gross evidence for leukemia was detected in all EL4 recipients of CD8-depleted or TCD A/J spleen cells, but only in one of 11 EL4 recipients of CD4-depleted A/IJ spleen cells. Together, the results in FIGS. 5 and 6 and Table 3 indicate that GVL effects are CD8-dependent and relatively CD4-independent in both IL-12-treated and control recipients.

All literature and patent references cited herein are incorporated by reference as if fully set forth.

TABLE 1

IL-12 mediated GVL effects while GVHD is inhibited in EL4 recipients

| Group (n) | Treatment | | Syngeneic Cells | | Allogeneic Cells | | MST (days) | Tumor at Autopsy (No. With Tumor/ Total Evaluated) |
|---|---|---|---|---|---|---|---|---|
| | EL4 | IL-12 | BMC | SPC | BMC | SPC | | |
| Expt. 1 | | | | | | | | |
| 1 (6) | − | +/− | + | + | − | − | >100 | 0/6 |
| 2 (9) | − | − | + | − | + | + | 41 | 0/7 |
| 3 (10) | − | + | + | − | + | + | 49 | 0/5 |
| 4 (5) | + | − | + | + | − | − | 18 | 4/4 |
| 5 (5) | + | + | + | + | − | − | 19 | 5/5 |
| 6 (10) | + | + | + | − | + | + | 50 | 0/5 |
| Expt. 2 | | | | | | | | |
| 1 (6) | − | +/− | + | + | − | − | >100 | 0/6 |
| 2 (8) | − | − | + | − | + | + | 36 | 0/4 |
| 3 (8) | − | + | + | − | + | + | >100 | 0/3 |
| 4 (5) | + | − | + | + | − | − | 23 | 4/4 |
| 5 (5) | + | + | + | + | − | − | 24 | 4/4 |
| 6 (9) | + | + | + | − | + | + | >100 | 0/6 |
| Expt. 3 | | | | | | | | |
| 1 (6) | − | +/− | + | + | − | − | >100 | 0/6 |
| 2 (8) | − | − | + | − | + | + | 7 | 0/3 |
| 3 (8) | − | + | + | − | + | + | 44 | 0/4 |
| 4 (5) | + | − | + | + | − | − | 21 | 4/5 |
| 5 (5) | + | + | + | + | − | − | 19 | 4/4 |
| 6 (8) | + | − | + | − | + | + | 8 | 0/5* |
| 7 (8) | + | + | + | − | + | + | 51 | 0/4 |

*All animals died of GVHD by 8 days post transplant.

TABLE 2

Role of IFN-γ in the GVL effect of allogeneic spleen cells in IL-12-treated mice

| Group (n) | Survival (%) Day 10 | Survival (%) Day 35 | Survival (%) Day 64 | Tumor at autopsy (No. with tumor/total evaluated) |
|---|---|---|---|---|
| Syn. BMT (3) | 100 | 100 | 100 | 0/3 |
| Syn. BMT, EL4 (5) | 100 | 0 | 0 | 5/5 |
| Allo. BMT (8) | 38 | 13 | 0 | 0/7 |
| Allo. BMT, IL-12 (7) | 100 | 86 | 75 | 0/8 |
| Allo. BMT, IL-12, R46A2* (8) | 100 | 50 | 12 | 0/7 |
| Allo. BMT, IL-12, EL4 (9) | 100 | 100 | 56 | 0/8 |
| Allo. BMT, IL-12, R4-6A2, EL4 (9) | 100 | 33 | 11 | 4/9 |

*R4-6A2: neutralizing rat anti-mouse IFN-γ mAb, 2.5 mg given i.p. on day 1.

TABLE 3

Autopsy analysis of EL4 recipients reconstituted with CD8-depleted and non-CD8-depleted A/J spleen cells

| BMT inocula | Tumor at autopsy (No. With tumor/No. Evaluated) |
|---|---|
| TCD B10 BMC (Syngeneic control) | 3/3 |
| TCD B10 BMC + TCD A/J BMC + CD8-depleted A/J SPC | 2/2 |
| TCD B10 BMC + TCD A/J BMC + CD8-depleted A/J SPC + IL-12 | 5/5 |
| TCD B10 BMC + TCD A/J BMC + TCD A/J SPC | 5/5 |
| TCD B10 BMC + TCD A/J BMC + TCD A/J SPC + IL-12 | 6/6 |
| TCD B10 BMC + TCD A/J BMC + CD4-depleted A/J SPC | 0/4 |
| TCD B10 BMC + TCD A/J BMC + CD4-depleted A/J SPC + IL-12 | 1/7 |

*. All animals were lethally irradiated whine 4–8 hours before BMF, and injected with 500 EL4 cells along with BMC and spleen cells.

†. No. of cells administered: TCD B1O BMC: $5\times10^6$; TCD A/J BMC: $10\times10^6$; CD8-depleted SPC: $12\times10^6$; CD4-depleted and TCD A/J SPC: $15\times10^6$.

What is claimed is:

1. A method of preventing graft-versus-host disease which comprises administering to a mammal, at the time of bone marrow transplantation, a therapeutically effective amount of interleukin-12 wherein said therapeutically effective amount is also effective to maintain or promote graft-vs.-leukemia effetcs in said mammal.

2. The method of claim 1, wherein the therapeutically effective amount of interleukin-12 comprises 1 to 100 µg/kg body weight.

3. The method of claim 2, wherein the interleukin-12 is administered for three days beginning on the day of the bone marrow transplant.

4. A method of ameliorating graft-versus-host disease which comprises administering to a mammal, at the time of bone marrow transplantation, a therapeutically effective amount of interleukin-12 wherein said therapeutically effective amount is also effective to maintain or promote graft-vs.-leukemia effetcs in said mammal.

5. The method of claim 4, wherein the therapeutically effective amount of interleukin-12 comprises 1 ng to 100 µg/kg body weight.

6. The method of claim 5, wherein the interleukin-12 is administered for three days beginning on the day of the bone marrow transplant.

7. A method of treating graft-versus-host disease which comprises administering to a mammal experiencing graft-versus-host disease a therapeutically effective amount of interleukin-12 wherein said therapeutically effective amount is also effective to maintain or promote graft-vs.-leukemia effetcs in said mammal.

8. The method of claim 7, wherein the therapeutically effective amount of interleukin-12 comprises 1 to 100 µg/kg body weight.

9. The method of claim 8, wherein the interleukin-12 is administered daily until improvement of the acute graft-versus-host disease is observed.

10. The method of claim 8, wherein the interleukin-12 is administered daily until remission of the graft-versus-host disease is observed.

11. A method of maintaining or promoting graft-vs.-leukemia effects which comprises administering to a mammal, at the time of bone marrow transplantation, a therapeutically effective amount of interleukin-12.

12. The method of claim 11, wherein the therapeutically effective amount of interleukin- 12 comprises 1 to 100 µg/kg body weight.

13. The method of claim 11 wherein said therapeutic dose is also effective to prevent, ameliorate or treat graft-vs.-host disease resulting from said transplantation.

* * * * *